(12) United States Patent
Chobotov

(10) Patent No.: US 6,395,019 B2
(45) Date of Patent: *May 28, 2002

(54) ENDOVASCULAR GRAFT

(75) Inventor: Michael V. Chobotov, Santa Rosa, CA (US)

(73) Assignee: TriVascular, Inc., Santa Rosa, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/133,978

(22) Filed: Aug. 14, 1998

Related U.S. Application Data

(60) Provisional application No. 60/074,112, filed on Feb. 9, 1998.

(51) Int. Cl.⁷ .............................................. A61M 29/00
(52) U.S. Cl. ...................... 623/1.13; 606/198; 623/1.36
(58) Field of Search ............................ 606/1, 108, 191, 606/194, 198; 623/1.1, 1.23, 1.25, 1.37, 1.35, 1.36

(56) References Cited

U.S. PATENT DOCUMENTS

| | | |
|---|---|---|
| 3,818,511 A | 6/1974 | Goldberg et al. .................. 3/1 |
| 3,902,198 A | 9/1975 | Rathjen ............................. 3/1 |
| 3,991,797 A | 11/1976 | Miller, Jr. et al. |
| 4,140,126 A | 2/1979 | Choudhury |
| 4,183,102 A | 1/1980 | Guiset ............................ 3/1.4 |
| 4,187,390 A | 2/1980 | Gore ........................... 174/102 |
| 4,208,745 A | 6/1980 | Okita ............................. 3/1.4 |
| 4,459,252 A | 7/1984 | MacGregor ................ 264/46.9 |
| 4,474,630 A | 10/1984 | Planck et al. .............. 156/62.4 |

(List continued on next page.)

FOREIGN PATENT DOCUMENTS

| | | |
|---|---|---|
| EP | 0 407 566 | 1/1990 |
| EP | 0 480 667 | 4/1992 |
| EP | 0 646 151 | 6/1992 |

(List continued on next page.)

OTHER PUBLICATIONS

Blum et al. "Abdominal aortic aneurysms: preliminary technical and clinical results with trasfemoral placement of endovascular self–expanding stent–grafts" *Radiology* 198(1):25–31 (1996).

Blum et al. "Endoluminal stent–grafts for infrarenal abdominal aortic aneurysms" *N Engl J Med* 336(1):13–20 (1997).

Ernst "Current therapy for infrarenal aortic aneurysms" *N Engl J Med* 336(1):59–60 (1997).

(List continued on next page.)

*Primary Examiner*—Henry J. Recla
*Assistant Examiner*—William W. Lewis
(74) *Attorney, Agent, or Firm*—Heller Ehrman White & McAuliffe LLP

(57) ABSTRACT

An endovascular graft which is configured to conform to the morphology of the vessel to be treated and which is made from an inflatable structure having a proximal end with a proximal inflatable cuff and a distal end with a distal inflatable cuff. At least one elongated inflatable channel is disposed between and in fluid communication with fluid tight chambers of the inflatable cuffs which may contain rupture discs therebetween which can be configured to rupture at different pressures. A thin flexible barrier disposed between the inflatable cuffs and the elongated inflatable channel of the frame so as to form a tubular structure defining a longitudinal channel to confine a flow of blood or other fluid therethrough. The graft may also have an expansion member attached to the proximal end of the graft which is preferably made of linked expandable rings of pseudoelastic shape memory alloy which is self expanding and prevents axial displacement of the graft once it is deployed.

55 Claims, 9 Drawing Sheets

U.S. PATENT DOCUMENTS

| | | | |
|---|---|---|---|
| 4,497,074 A | 2/1985 | Rey et al. | 3/1 |
| 4,550,447 A | 11/1985 | Seiler, Jr. et al. | 623/1 |
| 4,552,707 A | 11/1985 | How | 264/24 |
| 4,562,596 A | 1/1986 | Kornberg | |
| 4,592,754 A | 6/1986 | Gupte et al. | |
| 4,617,932 A | 10/1986 | Kornberg | 128/334 |
| 4,647,416 A | 3/1987 | Seiler, Jr. et al. | 264/118 |
| 4,665,906 A | 5/1987 | Jervis | |
| 4,705,517 A | 11/1987 | DiPisa, Jr. | |
| 4,787,899 A | 11/1988 | Lazarus | 623/1 |
| 4,816,028 A | 3/1989 | Kapadia et al. | 623/1 |
| 4,941,870 A | 7/1990 | Okada et al. | 600/36 |
| 4,957,669 A | 9/1990 | Primm | 264/23 |
| 5,100,422 A | 3/1992 | Berguer et al. | 606/151 |
| 5,104,399 A | 4/1992 | Lazarus | 623/1 |
| 5,104,400 A | 4/1992 | Berguer et al. | 264/132 |
| 5,108,424 A | 4/1992 | Hoffman, Jr. et al. | 623/1 |
| 5,151,105 A | 9/1992 | Kwan-Gett | |
| 5,156,620 A | 10/1992 | Pigott | |
| 5,207,695 A | 5/1993 | Trout, III | |
| 5,219,355 A | 6/1993 | Parodi et al. | |
| 5,275,622 A | 1/1994 | Lazarus et al. | |
| 5,282,847 A | 2/1994 | Trescony et al. | |
| 5,316,023 A | 5/1994 | Palmaz et al. | |
| 5,330,528 A | 7/1994 | Lazim | |
| 5,344,444 A | 9/1994 | Glastra | 623/1 |
| 5,354,310 A | 10/1994 | Garnic et al. | |
| 5,360,443 A | 11/1994 | Barone et al. | |
| 5,366,504 A | 11/1994 | Andersen et al. | |
| 5,370,682 A | 12/1994 | Schmitt | |
| 5,370,691 A | 12/1994 | Samson | |
| 5,387,235 A | 2/1995 | Chuter | |
| 5,397,345 A | 3/1995 | Lazarus et al. | 623/1 |
| 5,405,379 A | 4/1995 | Lane | |
| 5,423,851 A | 6/1995 | Samuels | |
| 5,456,713 A | 10/1995 | Chuter | |
| 5,464,419 A | 11/1995 | Glastra | 606/194 |
| 5,464,449 A | 11/1995 | Ryan et al. | |
| 5,489,295 A | 2/1996 | Piplani et al. | |
| 5,507,769 A | 4/1996 | Marin et al. | |
| 5,507,770 A | 4/1996 | Turk | |
| 5,522,880 A | 6/1996 | Barone et al. | |
| 5,527,355 A | 6/1996 | Ahn | 623/1 |
| 5,529,653 A | 6/1996 | Glastra | 156/216 |
| 5,534,024 A | 7/1996 | Rogers et al. | |
| 5,536,274 A | 7/1996 | Neuss | |
| 5,554,180 A | 9/1996 | Turk | 623/1 |
| 5,562,724 A | 10/1996 | Vorwerk et al. | |
| 5,562,726 A | 10/1996 | Chuter | |
| 5,562,728 A | 10/1996 | Lazarus et al. | 623/1 |
| 5,575,817 A | 11/1996 | Martin | |
| 5,578,071 A | 11/1996 | Parodi | |
| 5,578,072 A | 11/1996 | Barone et al. | |
| 5,607,468 A | 3/1997 | Rogers et al. | |
| 5,607,478 A | 3/1997 | Lentz et al. | 623/12 |
| 5,609,624 A | 3/1997 | Kalis | 623/1 |
| 5,609,628 A | 3/1997 | Keranen | 623/1 |
| 5,628,783 A | 5/1997 | Quiachon et al. | |
| 5,628,788 A | 5/1997 | Pinchuk | |
| 5,632,840 A | 5/1997 | Campbell | 156/196 |
| 5,653,746 A | 8/1997 | Schmitt | |
| 5,662,700 A | 9/1997 | Lazarus | |
| 5,665,115 A | 9/1997 | Cragg | |
| 5,665,117 A | 9/1997 | Rhodes | |
| 5,667,523 A | 9/1997 | Bynon et al. | |
| 5,669,936 A | 9/1997 | Lazarus | |
| 5,676,671 A | 10/1997 | Inoue | |
| 5,676,696 A | 10/1997 | Marcade | |
| 5,676,697 A | 10/1997 | McDonald | |
| 5,683,449 A | 11/1997 | Marcade | |
| 5,683,453 A | 11/1997 | Palmaz | |
| 5,693,084 A | 12/1997 | Chuter | |
| 5,693,087 A | 12/1997 | Parodi | |
| 5,693,088 A * | 12/1997 | Lazarus | 606/195 |
| 5,697,968 A | 12/1997 | Rogers et al. | |
| 5,707,378 A | 1/1998 | Ahn et al. | 606/139 |
| 5,709,701 A | 1/1998 | Parodi | |
| 5,709,703 A | 1/1998 | Lukie et al. | |
| 5,718,159 A | 2/1998 | Thompson | |
| 5,718,973 A | 2/1998 | Lewis et al. | 428/36.5 |
| 5,720,776 A | 2/1998 | Chuter et al. | 623/1 |
| 5,733,325 A | 3/1998 | Robinson et al. | |
| 5,747,128 A | 5/1998 | Campbell et al. | 428/35.7 |
| 5,749,880 A | 5/1998 | Banas et al. | 606/198 |
| 5,769,887 A | 6/1998 | Brown et al. | |
| 5,785,679 A | 7/1998 | Abolfathi et al. | |
| 5,788,626 A | 8/1998 | Thompson | 600/36 |
| 5,800,512 A | 9/1998 | Lentz et al. | 623/12 |
| 5,827,320 A | 10/1998 | Richter et al. | |
| 5,843,158 A | 12/1998 | Lenker et al. | 623/1 |
| 5,843,160 A | 12/1998 | Rhodes | |
| 5,843,167 A | 12/1998 | Dwyer et al. | 623/1 |
| 5,843,170 A | 12/1998 | Ahn | 623/1 |
| 5,871,536 A | 2/1999 | Lazarus | 623/1 |
| 5,871,537 A | 2/1999 | Holman et al. | 623/1 |
| 5,926,650 A | 7/1999 | Suzuki et al. | 395/834 |
| 5,961,546 A | 10/1999 | Robinson et al. | 623/1 |
| 5,968,090 A | 10/1999 | Ratcliff et al. | 623/1 |
| 5,976,179 A | 11/1999 | Inoue | 623/1 |
| 5,976,650 A | 11/1999 | Campbell et al. | 428/35.7 |
| 5,984,956 A | 11/1999 | Tweden et al. | 623/1 |
| 5,993,481 A | 11/1999 | Marcade et al. | 623/1 |
| 6,004,347 A | 12/1999 | McNamara et al. | 623/1 |
| 6,007,575 A | 12/1999 | Samuels | 623/1 |
| 6,015,431 A | 1/2000 | Thornton et al. | 623/1 |
| 6,025,044 A | 2/2000 | Campbell et al. | 428/36.91 |
| 6,027,811 A | 2/2000 | Campbell et al. | 428/411.1 |
| 6,036,723 A | 3/2000 | Anidjar et al. | 623/1 |
| 6,053,943 A | 4/2000 | Edwin et al. | 623/1.25 |
| 6,059,823 A | 5/2000 | Holman et al. | 623/1 |
| 6,063,114 A | 5/2000 | Nash et al. | 623/1.36 |
| 6,098,630 A | 8/2000 | Papazoglou | 128/898 |
| 6,102,938 A | 8/2000 | Evans et al. | 623/1 |
| 6,102,940 A | 8/2000 | Robichon et al. | 623/1 |
| 6,110,198 A | 8/2000 | Fogarty et al. | 623/1.12 |
| 6,124,523 A | 9/2000 | Banas et al. | 623/11 |
| 6,126,685 A | 10/2000 | Lenker et al. | 623/1 |
| 6,132,459 A | 10/2000 | Piplani et al. | 623/1.13 |
| 6,143,015 A | 11/2000 | Nobles | 606/194 |
| 6,149,682 A | 11/2000 | Frid | 623/1.35 |
| 6,152,956 A | 11/2000 | Pierce | 623/1.13 |
| 6,153,292 A | 11/2000 | Bell et al. | 428/305.5 |
| 6,156,063 A | 12/2000 | Douglas | 623/1.12 |
| 6,165,211 A | 12/2000 | Thompson | 623/1.13 |
| 6,165,212 A | 12/2000 | Dereume et al. | 623/1.13 |
| 6,165,213 A | 12/2000 | Goicoechea et al. | 623/1.34 |
| 6,165,214 A | 12/2000 | Lazarus | 623/1.35 |
| 6,183,504 B1 | 2/2001 | Inoue | 623/1.11 |
| 6,210,435 B1 | 4/2001 | Piplani et al. | 623/1.35 |
| 6,221,102 B1 | 4/2001 | Baker et al. | 623/1.36 |

FOREIGN PATENT DOCUMENTS

| | | |
|---|---|---|
| EP | 0 646 365 A1 | 9/1994 |
| EP | 0 689 806 A2 | 12/1995 |
| EP | 0 775 472 | 11/1996 |
| WO | 90/08801 | 8/1990 |
| WO | 92/22604 | 12/1992 |
| WO | WO 95/03754 | 2/1995 |
| WO | WO 95/09585 | 4/1995 |
| WO | WO 95/09586 | 4/1995 |
| WO | WO 95/11720 | 5/1995 |

| | | |
|---|---|---|
| WO | 95/16406 | 6/1995 |
| WO | 97/07751 | 3/1997 |
| WO | 97/25938 | 7/1997 |
| WO | 97/27820 | 8/1997 |
| WO | 97/33533 | 9/1997 |
| WO | WO 97/41804 | 11/1997 |
| WO | 98/06355 | 2/1998 |
| WO | 98/10806 | 3/1998 |
| WO | 98/12989 | 4/1998 |
| WO | 98/33453 | 8/1998 |
| WO | 98/41167 | 9/1998 |
| WO | 98/44870 | 10/1998 |
| WO | 98/44873 | 10/1998 |
| WO | 99/11199 | 3/1999 |
| WO | 99/32051 | 7/1999 |
| WO | 99/39663 | 8/1999 |
| WO | 00/10487 | 3/2000 |
| WO | 00/33769 | 6/2000 |

OTHER PUBLICATIONS

Moore et al. "Transfemoral endovascular repair of abdominal aortic aneurysm: results of the North American EVT phase 1 trial" *J Vasc Surg* 23(4):543–553 (1996).

Parodi et al. "Transfemoral intraluminal graft implantation for abdominal aortic aneurysms" *Ann Vasc Surg* 5(6):491–499 (1991).

Parodi "Endovascular repair of abdominal aortic aneurysms and other arterial lesions" *J Vasc Surg* 21(4):549–557 (1995).

* cited by examiner

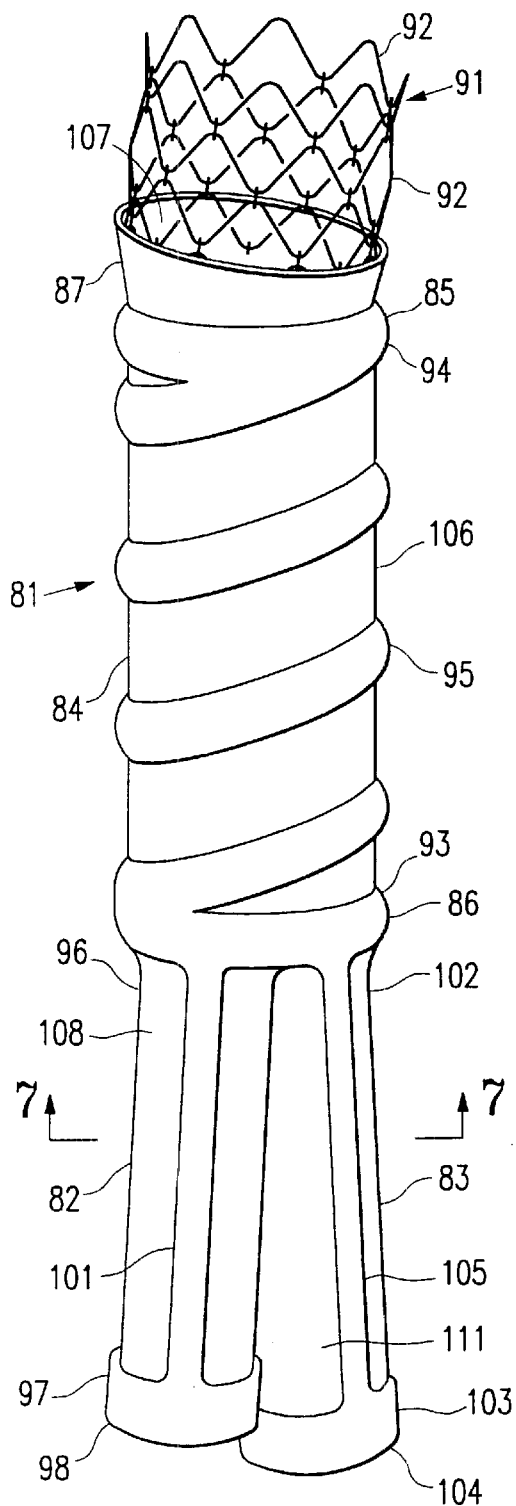
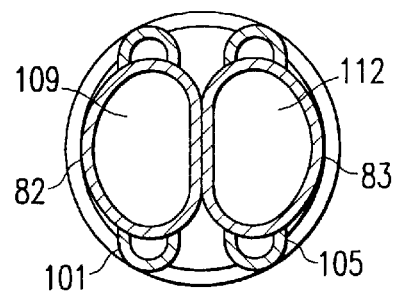
FIG. 6
FIG. 7

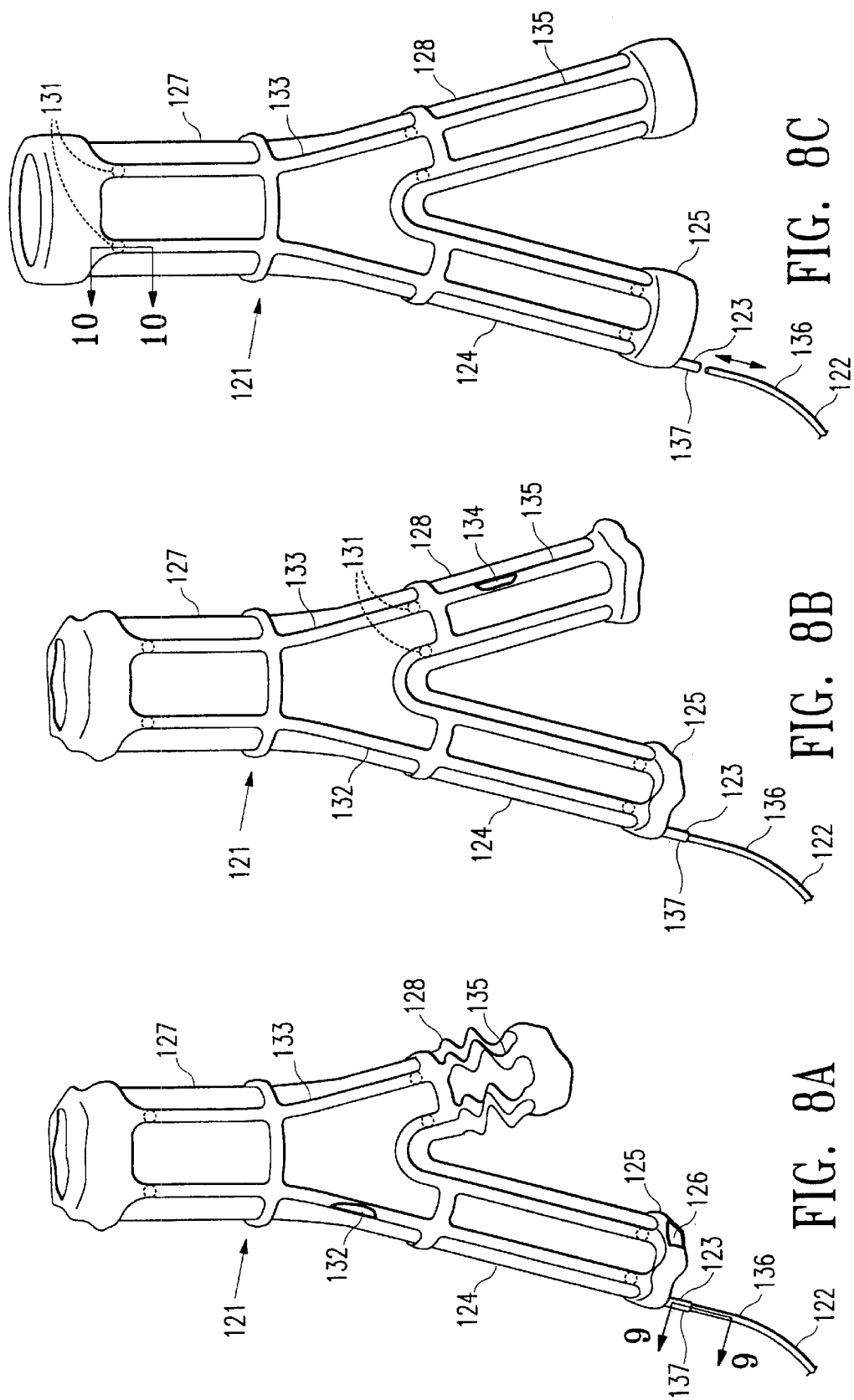

ENDOVASCULAR GRAFT

RELATED APPLICATIONS

This application is a continuation-in-part of Provisional Application Ser. No. 60/074,112, filed Feb. 9, 1998. Priority is hereby claimed to Provisional Application Ser. No. 60/074,112, which also incorporated by reference in its entirety herein.

BACKGROUND OF THE INVENTION

The present invention relates to a system and method for the treatment of disorders of the vasculature. More specifically, the present invention relates to a system and method for treatment of abdominal aortic aneurysm and the like, which is a condition manifested by expansion and weakening of the aorta below the diaphragm. Such conditions require Intervention due to the severity of the sequelae, which frequently is death. Prior methods of treating aortic aneurysm have consisted of invasive surgical methods with graft placement within the aorta as a reinforcing member of the artery. However, such a procedure requires a surgical cut down to access the vessel, which in turn can result in a catastrophic rupture of the aneurysm due to the decreased external pressure from the organs and tissues surrounding the aorta, which are moved during the procedure to gain access to the vessel. Accordingly, surgical procedures have a high mortality rate due to the possibility of the rupture discussed above in addition to other factors. Such other factors can include poor physical condition of the patient due to blood loss, anuria, and low blood pressure associated with the aortic abdominal aneurysm. An example of a surgical procedure is described in a book entitled *Surgical Treatment of Aortic Aneurysms* by Denton A. Cooley, M.D., published in 1986 by W. B. Saunders Company.

Due to the inherent risks and complexities of surgical procedures, various attempts have been made In the development of alternative methods for deployment of grafts within aortic aneurysms. One such method is the non-invasive technique of percutaneous delivery by a catheter-based system. Such a method is described in Lawrence, Jr. et al in "Percutaneous Endovascular Graft: Experimental Evaluation", *Radiology* (May 1987). Lawrence described therein the use of a Gianturco stent as disclosed in U.S. Pat. No. 4,580,568. The stent is used to position a Dacron fabric graft within the vessel. The Dacron graft is compressed within the catheter and then deployed within the vessel to be treated. A similar procedure has also been described by Mirich et at in "Percutaneously Placed Endovascular Grafts for Aortic Aneurysms: Feasibility Study", *Radiology* (March 1989). Mirich describes therein a self-expanding metallic structure covered by a nylon fabric, with said structure being anchored by barbs at the proximal and distal ends.

One of the primary deficiencies of the existing percutaneous devices and methods has been that the grafts and the delivery catheters used to deliver the grafts are relatively large in profile, often up to 24 French and greater, and stiff in bending. The large profile and bending stiffness makes delivery through the irregular and tortuous arteries of diseased vessels difficult and risky. In particular. the iliac arteries are often too narrow or irregular for the passage of a percutaneous device. Because of this, non-invasive percutaneous graft delivery for treatment of aortic aneurysm is not available to many patients who would otherwise benefit from it.

Another contraindication for current percutaneous grafting methods and devices is a vessel treatment site with high neck angulation which precludes a proper fit between the graft and the vessel wall. An improper fit or seal between the graft and the vessel wall can result in leaks or areas of high stress imposed upon the diseased vessel which lead to reduced graft efficacy and possibly rupture of the aneurysm.

While the above methods have shown some promise with regard to treating abdominal aortic aneurysms with non-invasive methods, there remains a need for an endovascular graft system which can be deployed percutaneously in a small diameter flexible catheter system. In addition, there is a need for a graft which conforms more closely to the contours of an aortic aneurysm which are often quite irregular and angulated and vary from patient to patient. The present invention satisfies these and other needs.

SUMMARY OF THE INVENTION

The present invention is directed generally to an endovascular graft for vascular treatment and a method for manufacturing and using the graft. The graft generally has an inflatable tubular frame structure which can be configured to conform to the morphology of a patient's vessel to be treated. The frame structure has a proximal end and a distal end with an inflatable cuff disposed on at least one end and preferably both. The inflatable cuffs can-be reduced in diameter and profile when deflated for introduction into a patient's vasculature by a catheter based delivery system or other suitable means. The inflatable cuffs provide a sufficiently rigid structure when inflated which supports the graft and seals the graft against the interior surface of the vessel in which it is being deployed. One or more elongated inflatable channels may also be disposed on the graft. Preferably, the elongated channel is disposed between and in fluid communication with a proximal and distal inflatable cuff. The channel provides the desired stiffness upon inflation, prevents kinking of the graft frame, and facilitates deployment of the graft within a patient's body passageway. The elongated inflatable channel can be in a longitudinal or linear configuration with respect to the graft, but is preferably shaped as a helix disposed about the graft. Other orientations such as interconnecting grids or rings may also be suitable for the elongated channels. The inflatable cuffs and the elongated channel contain fluid tight chambers which are generally in fluid communication with each other but which may also be separated by valves or rupture discs therein to selectively control the sequence of inflation or deployment. The fluid tight chambers are typically accessed by an injection port which is configured to accept a pressurized source of gas, fluid, particles, gel or combination thereof and which is in fluid communication with at least one of the fluid tight chambers. A fluid which sets, hardens or gels over time can also be used. The number of elongated channels can vary with the specific configuration of the graft as adapted to a given indication, but generally, the number of channels ranges from 1 to 25, preferably 2 to about 8.

A proximal neck portion may be secured to the proximal inflatable cuff. The proximal neck portion has a flexible tubular structure that has a diameter similar to the proximal inflatable cuff. The proximal neck portion can be configured as a straight tubular section or can be tapered distally or proximally to an increased or decreased diameter. Preferably, the proximal neck portion is secured and sealed to the proximal inflatable cuff and tapers proximally to an increased diameter so as to engage the inside surface of a vessel wall which provides a sealing function in addition to that of the proximal inflatable cuff. Such a configuration also smoothes the transition for fluid flow from the vessel of a patient to the lumen or channel within the endovascular graft. The proximal neck portion has an inlet axis that preferably has an angular bias with respect to a longitudinal axis of the graft.

Preferably, the graft has a monolithic structure wherein the material that comprises the inflatable cuffs and channels extends between these elements in a thin flexible layer that defines a longitudinal lumen to confine a flow of blood or other fluid therethrough. Such a monolithic structure can be made from a variety of suitable polymers including PVC, polyurethane, polyethylene and fluoropolymers such as TFE, PTFE and ePTFE. Additional stiffness or reinforcement can be added to the graft by the addition of metal or plastic inserts or battens to the graft, which can also facilitate positioning and deployment of the graft prior to inflation of an inflatable portion of the graft.

In another embodiment, the graft has a thin flexible layer disposed over or between a proximal inflatable cuff, a distal inflatable cuff, and an elongated inflatable channel of the frame. The thin flexible layer is made of a material differing from the material of the cuffs or elongated channel. The barrier is shaped so as to form a tubular structure defining a longitudinal lumen or channel to confine a flow of blood therethrough. The flexible barrier may be made of a variety of suitable materials such as DACRON®, NYLON®, or fluoropolymers such as TEFLON® or the like.

An endovascular graft having features of the invention may be made in a tubular configuration of a flexible layer material such as Dacron, Nylon or fluoropolymers as discussed above. The inflatable cuffs and elongated channels are formed separately and bonded thereto. The inflatable cuffs and channels may also be made from the same layer material, i.e., Dacron, Teflon, or Nylon with a fluid impermeable membrane or bladder disposed within the cuff or channel so as to make it fluid tight. To limit permeability, the material in the regions of the cuffs and channels may also be treated with a coating or otherwise be processed by methods such as thermo-mechanical compaction.

In one embodiment of the invention, an expansion member is attached to the proximal end of the frame structure of the graft or to a proximal neck portion of the graft. Expansion members may also be attached to the distal end of the graft. Preferably, the expansion member is made of an expandable ring or linked expandable rings of pseudoelastic shape memory alloy which is self expanding and helps to mechanically anchor the proximal end of the graft to a body channel to prevent axial displacement of the graft once it is deployed. By having an expansion member which is distinct from the proximal cuff, the sealing function of the cuff, which requires supple conformation to the vessel wall without excessive radial force, can be separated from the anchoring function of the expansion member, which can require significant radial force. This allows each function to be optimized without compromising the function of the other. It also allows the anchoring function which can require more radial force on the vessel wall to be located more proximal from the aneurysm than the cuff, and therefor be positioned in a healthier portion of the vessel which is better able to withstand the radial force required for the anchoring function. In addition, the cuff and expansion members can be separated spatially in a longitudinal direction with the graft in a collapsed state for delivery which allows for a lower more flexible profile for percutaneous delivery. Such a configuration makes a collapsed delivery profile of 12–16 French possible, preferably below 12 French.

The expandable ring or rings of the expansion member may be formed in a continuous loop having a serpentine or zig-zag pattern along a circumference of the loop. Any other similar configuration could be used that would allow radial expansion of the ring. The expansion member may be made of suitable high strength metals such as stainless steel, Nitinol or other shape memory alloys, or other suitable high strength composites or polymers. The expansion member may be made from high memory materials such as Nitinol or low memory materials such as stainless steel depending on the configuration of the endovascular graft, the morphology of the deployment site, and the mode of delivery and deployment of the graft.

The expansion member preferably has an inlet axis which forms an inlet axis angle in relation to a longitudinal axis of the graft. The angled inlet axis allows the graft to better conform to the morphology of a patient's vasculature in patients who have an angulated neck aneurysm morphology. The inlet axis angle can be from about 0 to about 90 degrees, preferably about 20 degrees to about. 30 degrees. Some or all of the inlet axis angle can be achieved in a proximal neck portion of the graft, to which the expansion member may be attached. An expansion member or members may also be attached to the distal end of the graft.

In another embodiment of the invention, the graft may be bifurcated at the distal end of a main body portion of the graft and have at least two bifurcated portions with longitudinal lumens in fluid communication with a longitudinal lumen of the main body portion. The first bifurcated portion and second bifurcated portion can be formed from a structure similar to that of the main body portion with optional inflatable cuffs at either the proximal or distal end. One or more elongated channels can be disposed between the inflatable cuffs.

The size and angular orientation of the bifurcated portions can vary, however, they are generally configured to have an outer diameter that is compatible with the inner diameter of a patient's iliac arteries. The bifurcated portions can also be adapted to use in a patient's renal arteries or other suitable indication. The distal ends of the bifurcated portions may also have expansion members attached thereto in order to anchor or expand, or both anchor and expand said distal ends within the body passageway being treated. The expansion members for the distal ends of the bifurcated portions can have similar structure to the expansion member attached to the proximal end or proximal neck portion of the main body portion. The expansion members are preferably made from a shape memory material such as Nitinol.

In bifurcated embodiments of grafts having features of the invention which also have a biased proximal end which forms an inlet axis angle, the direction of the bias or angulation can be important with regard to achieving a proper fit between the graft and the morphology of the deployment site. Generally, the angular bias of the proximal end of the graft, proximal neck portion or proximal expansion member can be in any direction. Preferably, the angular bias is in a direction normal to a plane defined by a longitudinal axis of the main body portion, the first bifurcated portion and the second bifurcated portion.

In another embodiment of the invention, rupture discs or other temporary closures are placed between fluid tight chambers of the inflatable cuffs and elongated channel or channels of the graft and form a seal between the chambers. The rupture discs may be burst or broken if sufficient force or pressure is exerted on one side of a disc or temporary closure. Once the graft is located at the site to be treated within a body passageway of a patient, a pressurized gas, fluid or gel may be injected by an inflation catheter into one of the fluid tight chambers of the graft through an injection port. Injection of a pressurized substance into an inflatable cuff will cause the cuff to take a generally annular shape, although the cuff can conform to the shape of the vessel within which it is deployed, and exert a sufficient radial force outward against the inner surface of the body passageway to be treated in order to provide the desired sealing function.

Multiple rupture discs can be disposed in various locations of the graft and also be configured to rupture at different pressures or burst thresholds to facilitate deployment of the graft within a body passageway. In a particular bifurcated embodiment of the invention, the proximal inflatable cuff of the main body portion may be positioned proximal of a junction between the branch of the abdominal aorta and the iliac arteries of a patient. As the proximal cuff is deployed by injection of an appropriate substance into an injection port in fluid communication with the fluid tight chamber thereof, it will expand radially and become axially and sealingly fixed proximal to the bifurcation of the aorta. A rupture disc is located between the fluid tight chamber of the proximal cuff and the elongated inflatable channels so that the proximal cuff may be substantially deployed before the rupture disc bursts and the elongated channels begin to fill with the injected substance. The elongated channels then fill and become sufficiently rigid and expand to create a longitudinal lumen therein. As pressure is increased within the fluid tight chamber, a rupture disc between the fluid tight chamber of the elongated channels and a fluid tight chamber of the optional distal inflatable cuff or distal manifold of the main body portion will burst and the distal inflatable cuff or manifold will deploy and become pressurized. One of the bifurcated portions of the graft may then be deployed as a rupture disc sealing its fluid tight chamber from the distal inflatable cuff or manifold of the main body portion of the graft bursts as the inflation pressure is increased. Finally, the second bifurcated portion of the graft deploys after a rupture disc sealing its fluid tight chamber from the main body portion bursts.

An inflation catheter which is attached to and in fluid communication with the fluid tight chambers of the graft via an injection port disposed thereon, can be decoupled from the injection port after completion of inflation by elevating pressure above a predetermined level. The elevated pressure causes a break in a connection with the injection port by triggering a disconnect mechanism. Alternatively, the inflation catheter can be unscrewed from its connection. The injection port can include a check valve, seal or plug to close off the egress of inflation material once the inflation catheter has been decoupled. The injection port could also be glued or twisted to seal it off.

A graft having features of the invention may also be deployed by percutaneous delivery with a catheter based system which has an inflatable balloon member disposed within expansion members of the graft in a collapsed state. The graft is percutaneously delivered to a desired site. Once the graft is axially positioned, the inflatable member of the balloon may be expanded and the expansion members forced radially against the interior surface of a body channel within which it is disposed. The expansion members may also be self expanding from a constrained configuration once the constraint is removed. After the graft has been positioned by the catheter system, the inflatable cuff or cuffs and elongated channel or channels of the graft are pressurized.

These and other advantages of the invention will become more apparent from the following detailed description of the invention when taken in conjunction with the accompanying exemplary drawings.

BRIEF DESCRIPTION OF THE DRAWINGS

FIG. 6 is a perspective view of a bifurcated endovascular graft having features of the present invention.

FIG. 7 is a transverse cross-sectional view of a bifurcated portion of an endovascular graft taken at 7—7 of FIG. 6.

FIGS. 8A–8C depict perspective views of a bifurcated endovascular graft having features of the present invention in various stages of deployment.

DETAILED DESCRIPTION OF THE INVENTION

Figure 1:
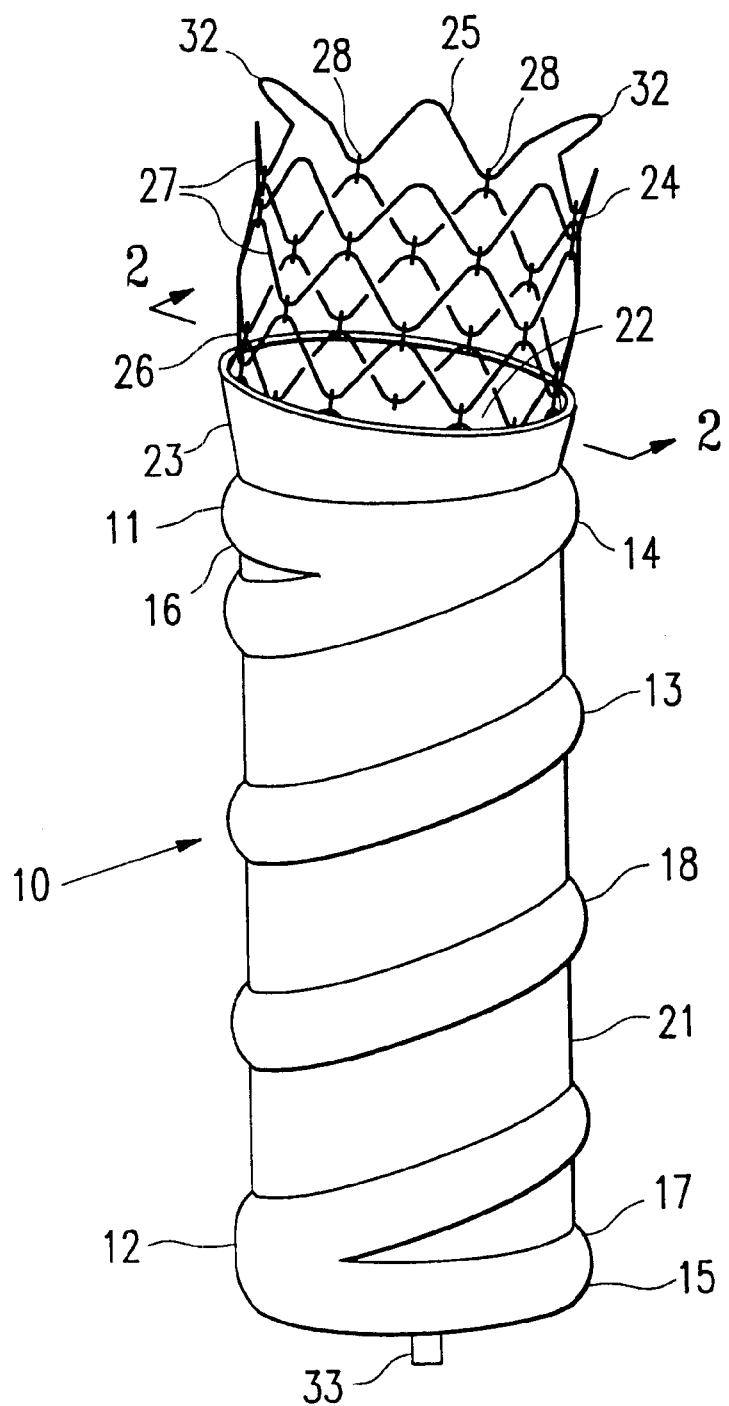
FIG. 1 shows a perspective view of an endovascular graft having features of the invention.

FIG. 1 shows a perspective view of an endovascular graft 10 having features of the present invention and having a proximal end 11 and a distal end 12. The graft is supported by an inflatable frame 13 which has a proximal end 14 and a distal end 15 and is shown in its deployed state. The inflatable frame structure 13 has a proximal inflatable cuff 16 at the proximal end 14 and an optional distal inflatable cuff 17 at the distal end 15. The inflatable cuffs 16 and 17 can be annular in shape when deployed, although the cuffs can conform to the shape of the vessel within which they are deployed, and can have an outside diameter or cross sectional dimension of about 10 to about 45 mm, preferably about 16 to about 28 mm. There is at least one elongated inflatable channel 18 disposed between the proximal inflatable cuff 16 and the distal inflatable cuff 17. The inflatable frame 13 can be from about 5 to about 30 cm in length, preferably about 10 to about 20 cm in length. Disposed between the proximal inflatable cuff 16, the distal inflatable cuff 17 and the elongated inflatable channel 18 is a thin flexible layer 21 that forms a longitudinal lumen 22 which can confine a flow of fluid therethrough. The thin flexible layer 21 may be made from the same material as the, inflatable cuffs 16 and 17 and elongated channel 18 and be integral with the construction of those elements forming a monolithic structure. The thin flexible layer 21 and the materials used to form the frame structure 13 can have a wall thickness of about 0.1 to about 0.5 mm, preferably about 0.15 to about 0.25 mm. The inflatable a frame 13 may be constructed from any suitable medical polymer or other material, including flouropolymers, PVCs, polyurethanes, PET, ePTFE and the like. Preferably the inflatable frame 13 and thin flexible layer 21 are made from ePTFE. A proximal neck portion 23 is attached to the proximal end of the inflatable frame structure 13 and serves as an additional means to seal the graft against the inside of a body passageway, provides a means of biasing a proximal end of the graft 11, and provides a smooth flow transition into longitudinal lumen 22.

An expansion member 24 having a proximal end 25 and a distal end 26 has the distal end secured to the proximal end 14 of the frame 13. The distal end 26 of the expansion member may also be secured to the proximal neck portion 23. The expansion member 24 can be made from expandable rings 27 formed in a zig-zag pattern and connected by links 28. The expansion member 24 is preferably a self-expanding member that expands to contact the inside wall of a body passage upon release from a constrained state. The expansion member 24 may be made from any suitable material that permits expansion from a constrained state, preferably a shape memory alloy such as Nitinol. The expansion member 24 may be configured to self expand from a constrained state or be configured to expand as a result of an outward radial force applied from within. Other materials suitable for construction of the expansion member 24 include stainless steel, MP35N alloy, shape memory alloys other than Nitinol, fiber composites and the like. The links 28 allow articulation of the expansion member 24 to traverse curvature of a patient's anatomy both during delivery and in situ. The expansion member 24 has a generally cylindrical shape but may also have outwardly directed protuberances 32 that are designed to engage the inside surface of a body passage. The expansion member 24 is generally cylindrical in shape when deployed, although the expansion member can conform to the shape of the vessel within which it is deployed, and can have a length of about 0.5 to about 5 cm, preferably about 1 to about 4 cm. The diameter of the expansion member 24 is typically similar to that of the inflatable cuffs 16 and 17, and can be about 10 to about 35 mm, preferably about 16 to about 28 mm. The high strength material from which the expansion member 24 is made can have a cross sectional dimension of about 0.1 to about 1.5 mm, preferably about 0.25 to about 1 mm.

The graft 10 is generally deployed by inflation of the inflatable frame structure 13 with a pressurized material of solid particles, gas, fluid or gel which can be injected through an injection port 33. The pressurized material may contain a contrast medium which facilitates imaging of the device while being deployed within a patient's body. For example, radiopaque materials such as bismuth, barium, gold, platinum, tantalum or the like may be used in particulate or powder form to facilitate visualization of the graft under fluoroscopy. Fixed radiopaque markers may also be attached or integrally molded into the graft for the same purpose, and may be made from the same radiopaque materials discussed above.

Figure 2:
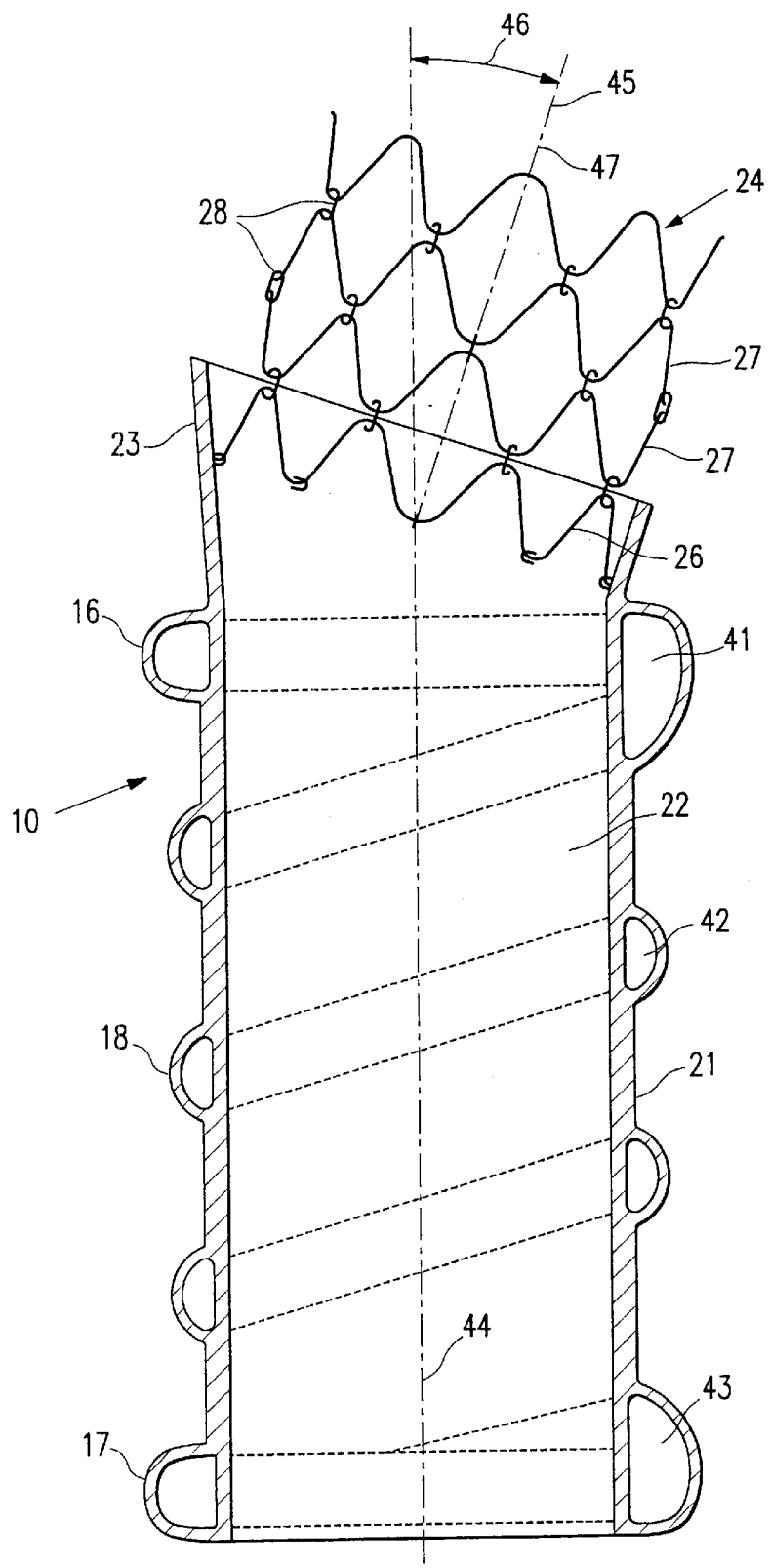
FIG. 2 shows a longitudinal cross sectional view of an endovascular graft having a monolithic structure.

FIG. 2 shows a longitudinal cross sectional view of the endovascular graft shown in FIG. 1. Within the proximal inflatable cuff 16 is a fluid tight chamber 41 which is in fluid communication with a fluid tight chamber 42 of the elongated inflatable channel 18. The fluid tight chamber 42 of the elongated inflatable channel is in fluid communication with a fluid tight chamber 43 within the optional distal inflatable cuff 17. A longitudinal axis 44 of the graft 10 is shown in addition to a proximal inlet axis 45 which forms an inlet axis angle 46 with the longitudinal axis. The angled inlet axis 45 is generally created by the proximal neck portion 23 and provides the graft with a profile which can conform to the morphology of a patient's vasculature. The expansion member 24 has a longitudinal axis 47 which is generally coextensive with the proximal inlet axis 45, but can further bend to conform to local anatomy including neck angulation of a diseased vessel.

Figure 3:
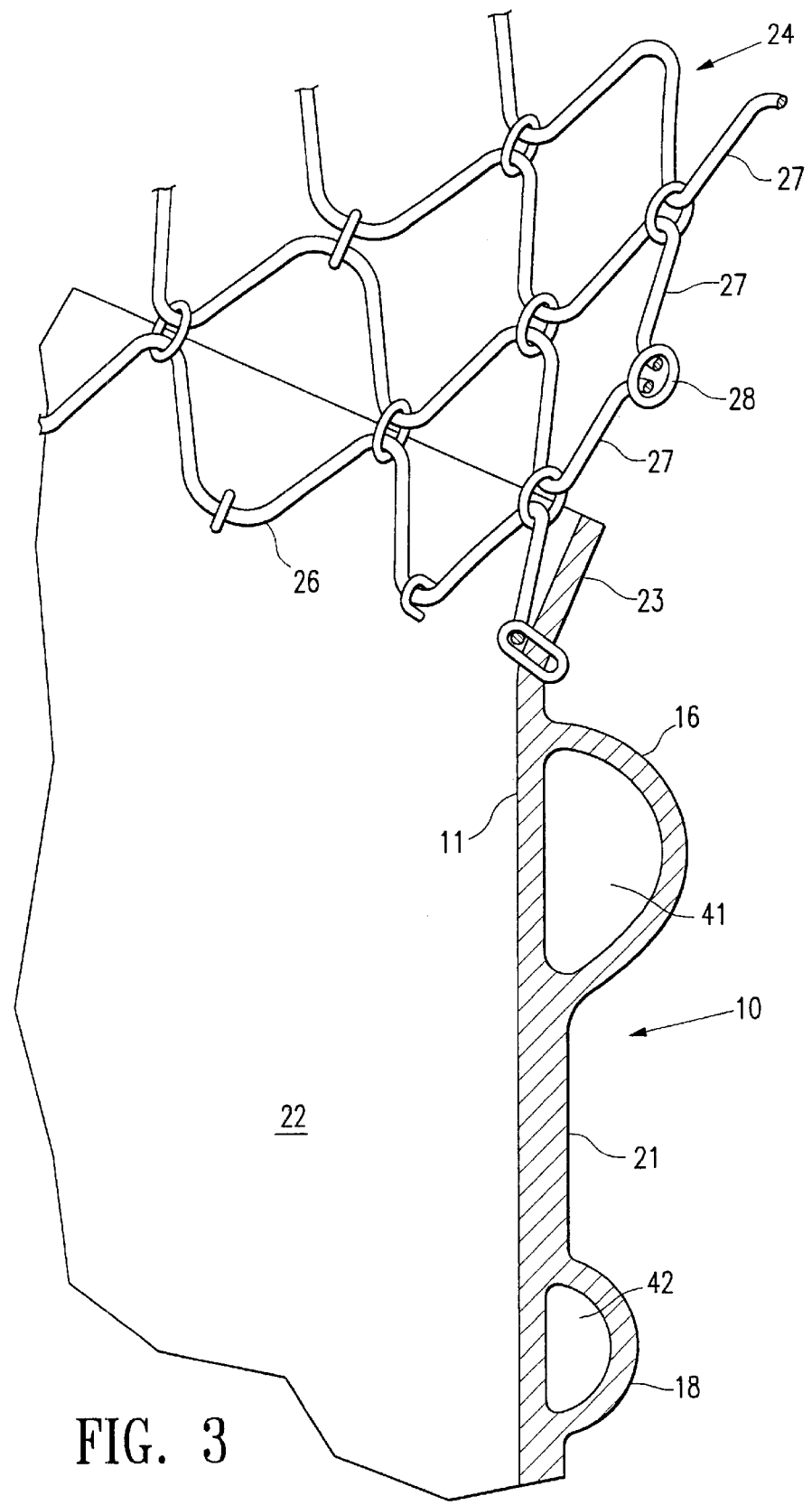
FIG. 3 shows an enlarged view of the longitudinal cross sectional view of the endovascular graft of FIG. 2.

FIG. 3 shows an enlarged view of the longitudinal cross sectional view of a portion of the proximal end 11 of the graft 10 shown in FIG. 2. A more detailed view of the fluid tight chamber 41 of the proximal inflatable cuff 16 can be seen as well as a more detailed view of the attachment of the distal end 26 of the expansion member 24 to the proximal neck portion 23. The thin flexible layer 21 can be seen disposed between the proximal inflatable cuff 16 and the elongated inflatable channel 18. The expandable rings 27 of the expansion member 24 are connected by links 28 which can be made from the same material as the expansion member or any other suitable material such as a biocompatible fiber or a metal such as stainless steel or Nitinol.

Figure 4:
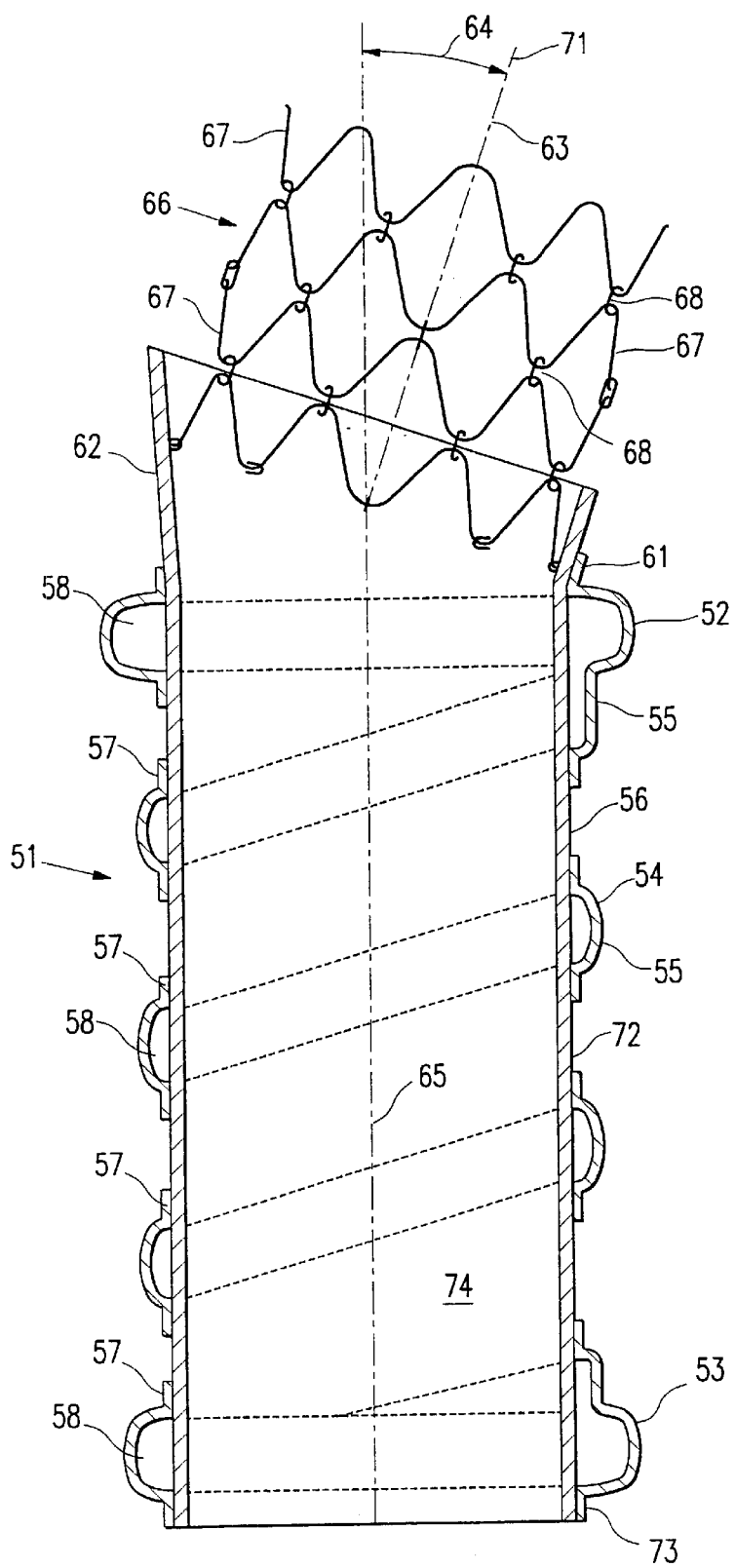
FIG. 4 shows a longitudinal cross-sectional view of an endovascular graft having features of the invention.

FIG. 4 is a transverse cross-sectional view of an embodiment of an endovascular graft 51, having features of the invention. The proximal inflatable cuff 52, distal inflatable cuff 53, and elongated inflatable channel 54 are formed by sealingly bonding strips of material 55 over a tubular structure 56. The strips 55 are bonded at the edges 57 so as to form fluid tight chambers 58 therein. If the material of the strips 55 which have been bonded to the tubular structure 56 are of a permeable character, an additional material may be used to coat the inside of the fluid tight chambers in order to make them impermeable to fluids. Alternatively, the material of the strips 55 and the material of the elongated tubular member 56 adjacent thereto may be made impermeable by undergoing further thermal, mechanical, or chemical processing. Preferably, thermo-mechanical compaction would be used to render the fluid tight chambers 58 impermeable to fluids which would be suitable for inflating the graft 51.

The proximal end 61 of the graft 51 has a proximal neck portion 62 which has an inlet axis 63 which forms an inlet axis angle 64 with a longitudinal axis 65 of the graft. The inlet axis angle 64 allows the graft 51 to better conform to a morphology of a patient's vascular channels. An expansion member 66 is also located at the proximal end 61 of the graft 51 and is formed of expandable rings 67 held together by links 68. The expansion member 66 has a longitudinal axis 71 which can coincide with the inlet axis 63 of the proximal neck portion 62. The graft 51 has a thin flexible layer 72 which extends from the distal end 73 of the graft 51, to the proximal end of the graft 61, including the proximal neck portion 62. The thin flexible layer 72 forms a longitudinal lumen or channel 74 upon deployment of the graft, which confines a flow of blood or other bodily fluid therethrough.

Figure 5:
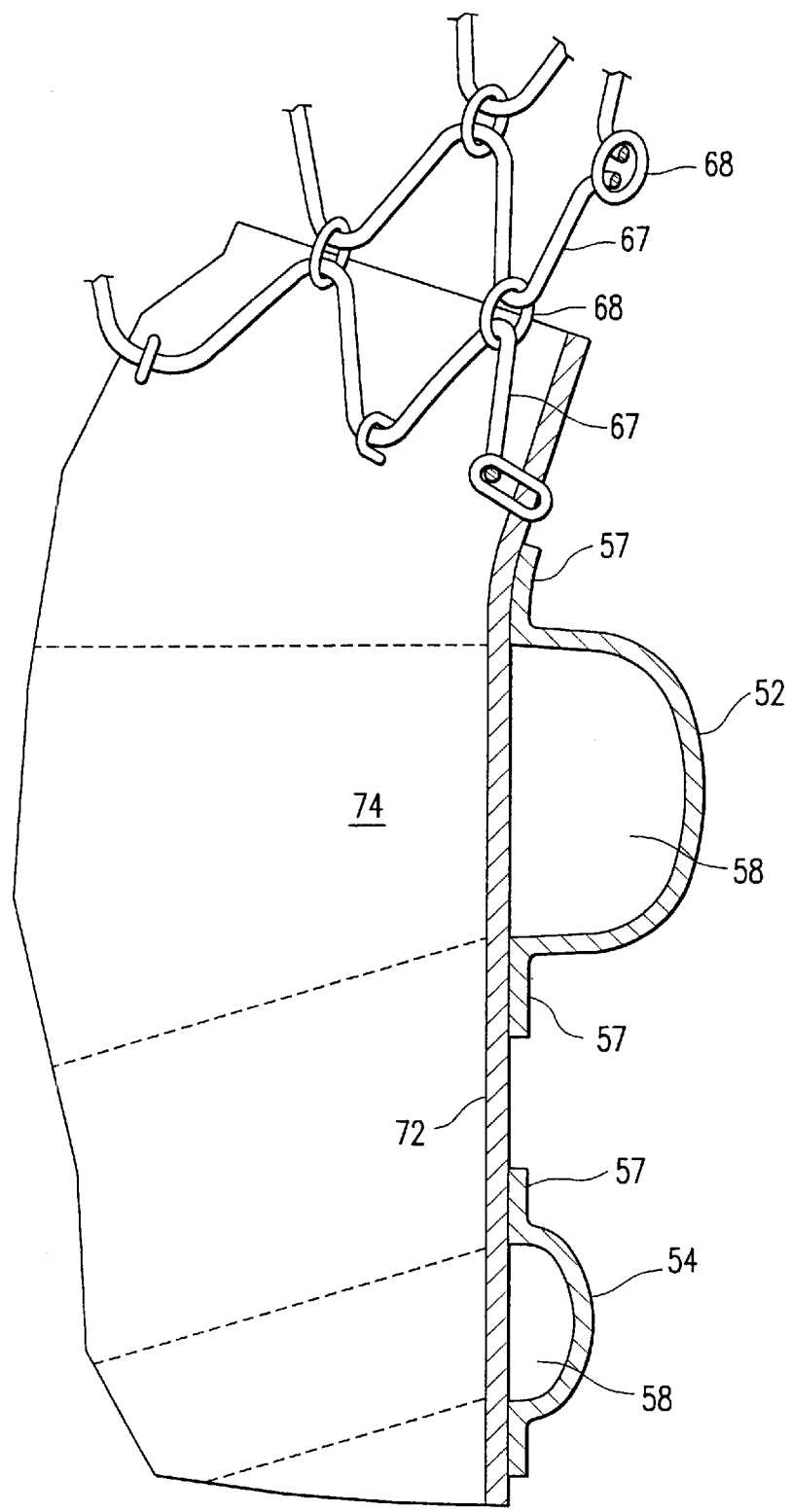
FIG. 5 shows an enlarged view of a portion of the endovascular graft shown in FIG. 4.

FIG. 5 is an enlarged view of the longitudinal cross-sectional view of the endovascular graft of FIG. 4. A more detailed view of the fluid tight chamber 58 of the proximal inflatable cuff and elongated inflatable channel can be seen. The edges of the strips 57 which form the proximal inflatable cuff 52 and the elongated inflatable channel 54 are bonded at the edges by any suitable technique such as the use of adhesives, solvents, or heat. Suitable adhesives would include epoxies and cyanoacrylates or the like. Materials suitable for use as the thin flexible layer 72 or the strips 55 includes Dacron, Nylon, Teflon, and also such materials as PVC, polyethylene, polyurethane and ePTFE.

FIGS. 6 and 7 depict an endovascular graft 81 having features of the invention which has a first bifurcated portion 82 and a second bifurcated portion 83. A main body portion 84 of the graft 81 has a proximal end 85 and a distal end 86 with a proximal neck portion 87 disposed at the proximal end as well as an expansion member 91 which can be formed of expandable rings 92 of a suitable material which have been linked together. At the distal end 86 of the main body portion 84 there is an optional distal inflatable cuff 93 which is connected fluidly to a proximal inflatable cuff 94 by an elongated inflatable channel 95. The distal inflatable cuff 93 may optionally be replaced by a manifold or other suitable structure for fluid connection between the elongated inflatable channel 95 and the first bifurcated portion 82 or the second bifurcated portion 83.

The first bifurcated portion 82 has a proximal end 96 and a distal end 97 with an optional distal inflatable cuff 98 located at the distal end. The distal end of the first bifurcated portion 97 may have an expansion member in conjunction with or in place of the distal inflatable cuff 98. The proximal end 96 of the first bifurcated portion 82 is attached to the distal end 86 of the main body portion 84 of the graft 81. The first bifurcated portion 82 has an optional inflatable elongated channel 101 which fluidly connects the distal inflatable cuff 98 of the first bifurcated portion 82 with the distal inflatable cuff 93 of the main body portion 84. The inflatable elongated channel 101 also provides support for first bifurcated portion 82.

The second bifurcated portion 83 generally has a structure similar to that of the first bifurcated portion 82, with a proximal end 102 and a distal end 103. The distal end 103 has an optional distal inflatable cuff 104. The proximal end 102 of the second bifurcated portion 83 is connected to the distal end 86 of the main body portion 84 of the graft 81. The distal end of the second bifurcated portion 103 may have an expansion member in conjunction with or in place of the distal inflatable cuff 104. The second bifurcated portion 83 has an optional inflatable elongated channel 105 which fluidly connects the distal inflatable cuff 104 of the second bifurcated portion 83 with the distal inflatable cuff 93 of the main body portion 84. The inflatable elongated channel 105 also provides support for the second bifurcated portion 83. The inflatable elongated channel of the first bifurcated portion 101 and inflatable elongated channel of the second bifurcated portion 105 may have a linear configuration as shown, a helical configuration similar to the main body portion 84, or any other suitable configuration. Disposed between the proximal inflatable cuff 94, distal If inflatable cuff 93 and elongated inflatable channel 95 of the main body portion 84 of the graft 81 is a thin flexible layer 106 which forms a longitudinal lumen 107 to confine the flow of blood or other bodily fluid therethrough. Disposed between the distal inflatable cuff 98 and the elongated inflatable channel 101 of the first bifurcated portion 82 and the distal inflatable cuff 93 of the main body portion 84 is a first thin flexible layer 108 which forms a longitudinal lumen 109 which is in fluid communication with the longitudinal lumen 107 of the main body portion 84. The second bifurcated portion may also be formed separate of a main body portion and be joined to the main body portion after percutaneous delivery thereof by docking methods. The first and second bifurcated portions 82 and 83 are generally cylindrical in shape when deployed, although they can conform to the shape of a vessel within which they are deployed, and can have a length from about 1 to about 10 cm. The outside diameter of the distal ends of the first and second bifurcated portions 82 and 83 can be from about 2 to about 30 mm, preferably about 5 to about 20 mm.

A second thin flexible layer 111 is disposed between the distal inflatable cuff 104 and elongated inflatable channel 105 of the second bifurcated portion 83 and the distal inflatable cuff 93 of the main body portion 84. The second thin flexible layer 111 forms a longitudinal lumen 112 which is in fluid communication with the longitudinal lumen 107 of the main body portion 84. The thin flexible layer of the first bifurcated portion surrounds the elongated lumen of the first bifurcated portion. The thin flexible layer of the second bifurcated portion surrounds the elongated lumen of the second bifurcated portion.

FIGS. 8A–8C depict an embodiment of an endovascular graft 121 having features of the invention in various stages of deployment. In FIG. 8A, an inflation catheter 122 is connected to an injection port 123 in a first bifurcated portion 124 of the endovascular graft 121. The injection port 123 is connected to a distal inflatable cuff 125 of the first bifurcated portion 124 and is in fluid communication with a fluid tight chamber 126 therein. The first bifurcated portion 124 and a main body portion 127 have been substantially inflated in FIG. 8A, however, a second bifurcated portion 128 has been prevented from deployment by rupture discs 131 which have been disposed within fluid tight chambers 132 of the elongated inflatable channels 133 of the main body portion 127 which are connected to fluid tight chambers 134 of elongated inflatable channels 135 of the second bifurcated portion 128. In FIG. 8B, the second bifurcated portion 128 has been substantially deployed subsequent to a rupture or bursting of the rupture discs 131 disposed within the fluid tight chambers 132 and 134 of the elongated inflatable channels 133 and 135 which permitted the flow of a pressurized substance therein. FIG. 8C shows the endovascular graft fully deployed and illustrates detachment of a distal end 136 of the inflation catheter 122 from the injection port 123 which is carried out by increasing the pressure within the inflation catheter until a disconnect mechanism 137 is triggered.

Figure 9A:
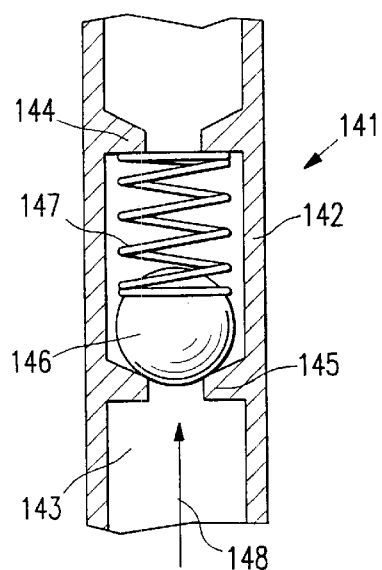
FIG. 9A is an enlarged longitudinal cross sectional view of the valve that could be used to maintain inflation of a fluid tight chamber in the endovascular graft taken at 9—9 of FIG. 8A.

FIG. 9A illustrates a longitudinal cross-sectional view taken at 9—9 of FIG. 8A. The one-way inflation valve 141 has an outer wall 142, an inner lumen 143, an annular spring stop 144, an annular ball seal 145, a sealing body 146 and a sealing spring 147. The configuration depicted in FIG. 9A allows for the ingress of an inflation medium in the direction of the arrow 148 while preventing an egress of same once pressure is removed.

Figure 9B:
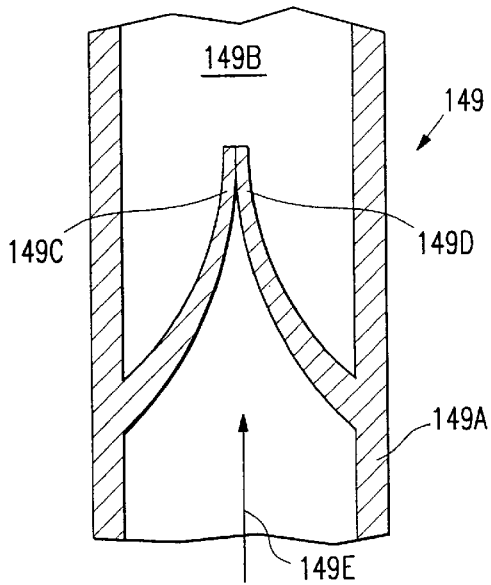
FIG. 9B is an enlarged longitudinal cross sectional view of an alternative seal that could be used to maintain inflation of a fluid tight chamber in the endovascular graft taken at 9—9 of FIG. 8A.

FIG. 9B illustrates an alternative one way valve. The one-way inflation valve 149 has an outer wall 149A, an inner lumen 149B, a first reed valve 149C, and a second reed valve 149D which is fluidly sealed with the first reed valve in a relaxed state. The configuration depicted in FIG. 9B allows for the ingress of an inflation medium in the direction of the arrow 149E while preventing an egress of same once pressure is removed.

Figure 9C:
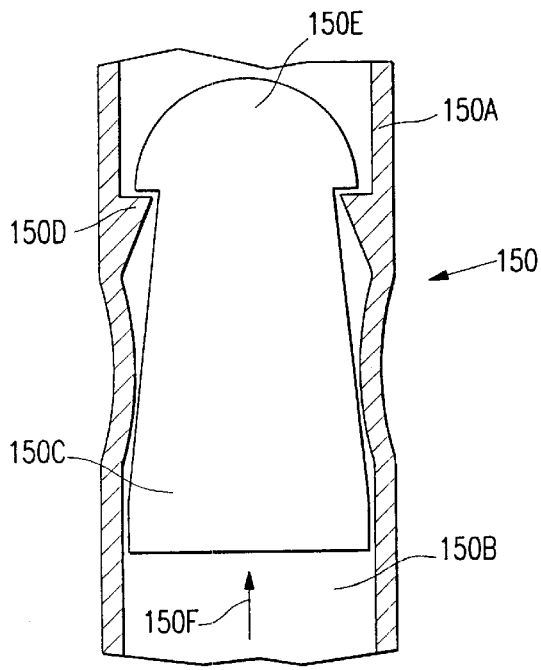
FIG. 9C is an enlarged longitudinal cross sectional view of an alternative sealing plug that could be used to maintain inflation of a fluid tight chamber in the endovascular graft taken at 9—9 of FIG. 8A.

FIG. 9C illustrates an alternative seal 150. The seal has an outer wall 150A, an inner lumen 150B, a plug 150C and a sealing surface 150D. The plug 150C has a sealing head 150E which sealingly engages the sealing surface 150D by irreversible deployment by application of force to the plug in the direction of the arrow 150F.

Figure 10:
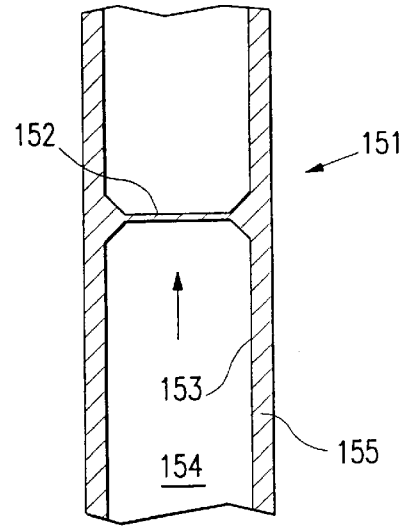
FIG. 10 is an enlarged longitudinal cross sectional view of a rupture disc that could be used to control the inflation sequence of an inflatable endovascular graft taken at 10—10 of FIG. 8C.

FIG. 10 depicts a longitudinal cross-sectional view of a rupture disc 151 taken at 10—10 of FIG. 8C. The rupture disc 151 has a wall member 152 which is sealingly secured to the inside surface 153 of a fluid tight chamber 154. The wall member 152 is configured to fail under pressure prior to the failure of the surrounding wall 155 of the fluid tight chamber 154 under pressure. The rupture disc 151 allows for deployment and inflation of fluid tight chambers other than those which have been sealed by the rupture disc. Once sufficient force or pressure is exerted against the wall 152 of the rupture disc to cause failure, the rupture disc 151 will burst and permit the ingress of an inflation medium and deployment of a portion of an inflatable graft, previously sealed by the rupture disc.

Figure 11:
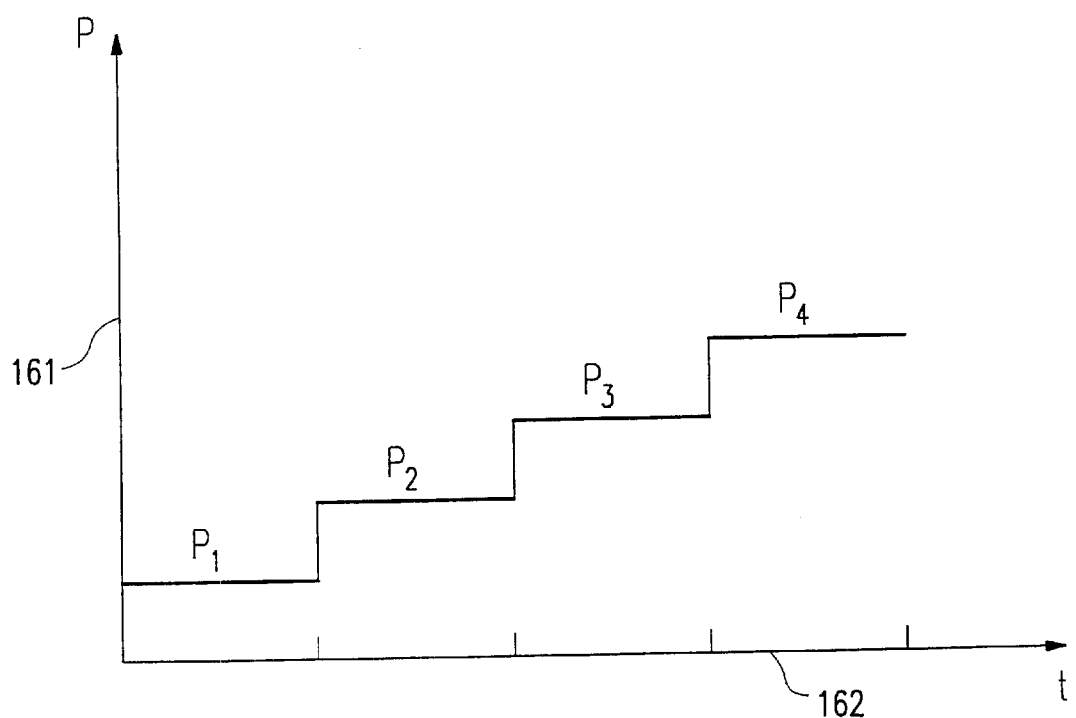
FIG. 11 is a plot of inflation pressure of an inflatable endovascular graft with respect to time for an endovascular graft having features of the present invention including rupture discs which are configured to yield at various predetermined pressures.

FIG. 11 depicts a graphical representation of inflation pressure 161 versus the time 162 at an injection port of an inflatable graft as depicted in FIGS. 8A–8C during the deployment process. $P_1$ represents the inflation pressure at the injection port prior to the rupturing of any rupture discs in the endovascular graft. $P_2$ represents the pressure required to cause failure or bursting of the weakest rupture disc in the endovascular graft after which a portion of the endovascular graft previously sealed by the weakest rupture disc is inflated and deployed. The pressure then increases over time to $P_3$ which is the pressure level required to cause failure or bursting of a second rupture disc. $P_4$ is the pressure level required for triggering a disconnect mechanism at the distal end of the inflation catheter.

While particular forms of the invention have been illustrated and described, it will be apparent that various modifications can be made without departing from the spirit and scope of the invention. Accordingly, it is not intended that the invention be limited, except as by the appended claims.

What is claimed is:

1. An endovascular graft comprising:
    a) a tubular structure having a first end portion and a second end portion;
    b) an inflatable cuff permanently secured to the tubular structure adjacent the first end portion; and
    c) a non-inflatable expansion member secured to and extending from the first end portion away from the tubular structure and configured to exert an outward radial force independent of the tubular structure.

2. The endovascular graft of claim 1 wherein the inflatable cuff is configured to sealingly engage an interior surface of a vessel wall.

3. The endovascular graft of claim 1 further comprising a neck portion at the first end portion having an inlet axis which forms an angle up to about 45 degrees with a longitudinal axis of the tubular structure.

4. The endovascular graft of claim 1 wherein the inflatable cuff is formed separately from the tubular structure and bonded thereto.

5. The endovascular graft of claim 1 wherein the inflatable cuff is integral with the tubular structure to form a monolithic structure.

6. The endovascular graft of claim 1 wherein the inflatable cuff is formed by bonding the edges of strips of material to the tubular structure.

7. The endovascular graft of claim 1 wherein the non-inflatable expansion member is self-expanding.

8. An endovascular graft comprising:
    a) an inflatable frame structure having a proximal end and a distal end, with a proximal inflatable cuff disposed on the proximal end and at least one elongated inflatable channel in fluid communication with the proximal inflatable cuff;
    b) a thin flexible layer member disposed between the proximal inflatable cuff, and the elongated inflatable channel of the frame to form a longitudinal channel; and
    c) a non-inflatable expansion member disposed proximal of the proximal inflatable cuff, secured to the proximal end of the inflatable frame structure, extending away from the inflatable frame structure and configured to exert an outward radial force independent of the inflatable frame structure.

9. The endovascular graft of claim 8 wherein the non-inflatable expansion member is comprised of linked expandable rings.

10. The endovascular graft of claim 9 wherein the linked expandable rings are comprised of a pseudoelastic shape memory alloy.

11. The endovascular graft of claim 10 wherein the linked expandable rings further comprise outwardly directed protuberances.

12. The endovascular graft of claim 8 further comprising a rupture disc disposed between a fluid tight chamber of the proximal inflatable cuff and a fluid tight chamber of the elongated channel.

13. The endovascular graft of claim 8 wherein the thin flexible layer is disposed over, at least partially surrounds, and is secured to the inflatable frame structure.

14. The endovascular graft of claim 8 wherein the thin flexible layer is disposed within and secured to the inflatable frame structure.

15. The endovascular graft of claim 8 further comprising a proximal neck portion secured to the proximal end of the inflatable frame structure.

16. The endovascular graft of claim 15 wherein the proximal neck portion tapers proximally to a reduced diameter.

17. The endovascular graft of claim 15 wherein the proximal neck portion tapers proximally to an increased diameter.

18. The endovascular graft of claim 8 further comprising a distal neck portion.

19. The endovascular graft of claim 18 wherein the distal neck portion tapers distally to a reduced diameter.

20. The endovascular graft of claim 18 wherein the distal neck portion tapers distally to an increased diameter.

21. The endovascular graft of claim 17 further comprising a distal neck portion that tapers distally to a increased diameter.

22. The endovascular graft of claim 15 wherein the proximal neck portion further comprises a proximal inlet axis which forms an inlet axis angle with a longitudinal axis of the endovascular graft of up to about 50 degrees.

23. The endovascular graft of claim 22 wherein the inlet axis angle is about 20 to about 30 degrees.

24. The endovascular graft of claim 8 wherein the non-inflatable expansion member is secured to the proximal end of the inflatable frame structure and has an inlet axis which forms an angle with respect to a longitudinal axis of the endovascular graft of up to about 40 degrees.

25. The endovascular graft of claim 8 wherein the non-inflatable expansion member is self-expanding.

26. An endovascular graft comprising:
    a) a tubular main body portion with a distal end, a proximal end, a proximal inflatable cuff disposed on the proximal end, a non-inflatable expansion member which is disposed proximally of the proximal inflatable cuff, secured to the proximal end extending away from the tubular main body portion and configured to exert an outward radial force independent of the tubular main body portion, at least one elongated inflatable channel in fluid communication with the proximal inflatable cuff, and a thin flexible layer disposed between the proximal inflatable cuff and elongated inflatable channel so as to form a conduit to confine a flow of fluid therethrough;

b) a first bifurcated tubular portion having a distal end and a proximal end which is secured to the distal end of the tubular main body portion, and having a conduit therein extending from the proximal end to the distal end, said conduit in fluid communication with the conduit of the tubular main body portion; and c) a second bifurcated tubular portion having a distal end and a proximal end which is secured to the distal end of the tubular main body portion, and having a conduit therein extending from the proximal end to the distal end, said conduit in fluid communication with the conduit of the tubular main body portion.

27. The endovascular graft of claim 26 wherein the non-inflatable expansion member is comprised of linked expandable rings.

28. The endovascular graft of claim 27 wherein the linked expandable rings are comprised of a pseudoelastic shape memory alloy.

29. The endovascular graft of claim 28 wherein the linked expandable rings further comprise outwardly directed protuberances.

30. The endovascular graft of claim 26 wherein a rupture disc is disposed between a fluid tight chamber of the proximal inflatable cuff and a fluid tight chamber of the elongate inflatable channel.

31. The endovascular graft of claim 30 wherein the first bifurcated tubular portion further comprises an elongated inflatable channel in fluid communication with the elongated inflatable channel of the tubular main body portion and the second bifurcated tubular portion further comprises an elongated inflatable channel in fluid communication with the elongated inflatable channel of the tubular main body portion.

32. The endovascular graft of claim 31 further comprising a rupture disc disposed between the fluid tight chamber of the elongated inflatable channel of the tubular main body portion and a fluid tight chamber of the elongated inflatable channel of the first bifurcated tubular portion.

33. The endovascular graft of claim 32 further comprising a rupture disc disposed between the fluid tight chamber of the elongated inflatable channel of the tubular main body portion and a fluid tight chamber of the elongated inflatable channel of the second bifurcated tubular portion.

34. The endovascular graft of claim 33 wherein the rupture discs have different burst thresholds to facilitate sequential deployment of the graft.

35. The endovascular graft of claim 26 further comprising a proximal neck portion disposed on the proximal end of the tubular main body portion.

36. The endovascular graft of claim 35 wherein the proximal neck portion tapers proximally to a reduced diameter.

37. The endovascular graft of claim 35 wherein the proximal neck portion tapers proximally to an increased diameter.

38. The endovascular graft of claim 26 wherein the proximal end of the tubular main body portion further comprises a proximal inlet axis which forms an inlet axis angle with respect to a longitudinal axis of the main body portion of up to about 50 degrees.

39. The endovascular graft of claim 38 wherein the inlet axis angle is about 20 to about 30 degrees.

40. The endovascular graft of claim 26 wherein the expansion member further comprises a proximal inlet axis which forms an inlet axis angle with respect to a longitudinal axis of the endovascular graft of about 20 to about 30 degrees.

41. The endovascular graft of claim 26 further comprising elongated battens disposed upon the graft.

42. The endovascular graft of claim 41 wherein the battens are comprised of metal or plastic.

43. The endovascular graft of claim 26 wherein the non-inflatable expansion member is self-expanding.

44. A method of deploying an endovascular graft comprising:

a) providing an inflatable endovascular graft comprising:
a tubular body member having a proximal end and a distal end;
a proximal inflatable cuff disposed on the proximal end of the tubular body member; and
a non-inflatable expansion member disposed proximally of the proximal inflatable cuff, secured to the proximal end of the tubular member extending away from the tubular body member and configured to exert an outward radial force independent of the tubular body member;

b) positioning the graft in a desired location within a body channel of a patient;

c) allowing the non-inflatable expansion member to expand to conform to a morphology of the body channel; and d) inflating the proximal inflatable cuff to form a seal against the body channel.

45. The method of claim 44 wherein inflation of the proximal inflatable cuff of the graft causes the graft and proximal inflatable cuff to conform to a morphology of the body channel surrounding the graft.

46. The method of claim 44 wherein the endovascular graft is positioned by percutaneous delivery.

47. The method of claim 44 wherein the non-inflatable expansion member is allowed to expand by extruding the graft from a constraining tubular delivery catheter.

48. The method of claim 44 wherein the endovascular graft further comprises a plurality of inflatable fluid tight chambers which are separated by rupture discs that are configured to burst at varying pressure thresholds such that the graft is sequentially inflated.

49. The method of claim 44 wherein the proximal inflatable cuff is inflated by injecting a pressurized material through an inflation catheter and into an injection port which is in fluid communication with a fluid tight chamber within the proximal inflatable cuff.

50. The method of claim 49 further comprising disconnecting the inflation catheter from the injection port by applying inflation pressure sufficient to trigger a disconnect mechanism.

51. An endovascular graft comprising:

a) an inflatable frame structure comprising:
a main body portion having
a proximal end with a proximal inflatable cuff disposed thereon,
a distal end with a distal inflatable cuff disposed thereon,
at least one elongated inflatable channel disposed between and in fluid communication with the proximal inflatable cuff and the distal inflatable cuff,
a first bifurcated portion having
a proximal end which is connected to the distal end of the main body portion, a proximal inflatable cuff disposed on the proximal end, a distal end with a distal inflatable cuff disposed thereon, at least one elongated inflatable channel disposed between and in fluid communication with the proximal inflatable cuff and the distal inflatable cuff, a second bifurcated portion having a proximal end which is connected to the distal end of the main body portion, a proximal inflatable cuff disposed on the proximal end, a distal end with a distal inflatable cuff disposed thereon, and at least one elongated inflatable channel disposed between and in fluid communication with the proximal inflatable cuff and the distal inflatable cuff; and b) a thin flexible layer member disposed between the proximal inflatable cuff, the distal inflatable cuff and the elongated inflatable channel of the main body portion, first bifurcated portion and second bifurcated portion in order to form a bifurcated tubular structure having a longitudinal channel to confine a flow of blood therethrough at each of said portions.

52. An endovascular graft comprising:
a) a tubular structure having a proximal end portion and a distal end portion;
b) an inflatable cuff disposed on the proximal end portion; and
c) a non-inflatable expansion member disposed proximal of the inflatable cuff, secured to the graft extending away from the tubular structure and configured to exert an outward radial force independent of the tubular structure.

53. The endovascular graft of claim 52 wherein the non-inflatable expansion member is secured to the inflatable cuff.

54. The endovascular graft of claim 52 further comprising a proximal neck portion wherein the non-inflatable expansion member is secured to the proximal neck portion.

55. The endovascular graft of claim 52 wherein the non-inflatable expansion member is self-expanding.

* * * * *